United States Patent [19]

Sorge

[11] Patent Number: 5,328,581
[45] Date of Patent: Jul. 12, 1994

[54] ELECTROPHORESIS TEMPERATURE FEEDBACK CONTROLLER

[75] Inventor: Joseph Sorge, La Jolla, Calif.
[73] Assignee: Stratagene, La Jolla, Calif.
[21] Appl. No.: 643,398
[22] Filed: Jan. 18, 1991
[51] Int. Cl.$^5$ .................. G01N 27/26; G01N 27/447; B01D 57/02
[52] U.S. Cl. .................. 204/182.8; 204/299 R
[58] Field of Search .................. 204/299 R, 182.8

[56] References Cited

U.S. PATENT DOCUMENTS 3,915,827 10/1975 Davies .................. 204/299 R X

Primary Examiner—John Niebling
Assistant Examiner—John S. Starsiak, Jr.
Attorney, Agent, or Firm—Lyon & Lyon

[57] ABSTRACT

A method of (and apparatus for) electrophoresis in which the gel temperature is controlled automatically. A sensor may measure a gel temperature and a processor may control a power supply for the electrophoresis process in response to that measurement. Measurements may be made at predetermined times (e.g., periodically) and the processor may determine control settings for the power supply based on a preferred temperature for the electrophoresis process. The preferred temperature for the electrophoresis process may be a predetermined temperature which is chosen so that the electrophoresis process operates at or near the highest speed which is unlikely to break the glass plates.

21 Claims, 8 Drawing Sheets

ELECTROPHORESIS TEMPERATURE FEEDBACK CONTROLLER

BACKGROUND OF THE INVENTION

1. Field of the Invention

This invention relates to electrophoresis, particularly to regulating gel temperature during gel electrophoresis.

2. Description of Related Art

Electrophoresis is a process for separating chemical substances from one another by means of their differential molecular weights. The chemical substances may be naturally charged, or a charge may be applied to them prior to electrophoresis. The chemical substances may be embedded in a neutral medium such as a gel. An electric potential is applied to the mixture for a fixed time period, during which lighter molecules will move more quickly. At the end of the period, the lighter molecules will have moved farther than the heavier molecules. Thus, one application of electrophoresis is to determine relative proportions of chemical substances in a mixture.

Electrophoresis is commonly used to determining the sequence of base pairs in nucleic acids such as deoxyribonucleic acid (DNA) or ribonucleic acid (RNA). This process is called "sequencing". Although sequencing may be done automatically by certain specialized equipment, but the cost of such equipment is too high for the average researcher. Manual sequencing is often tedious and time-consuming.

It has been found that electrophoresis is faster when performed with higher voltages; and that higher voltages generate heat which elevates the gel temperature. If the temperature rises too high, the glass plates which are used in the electrophoresis process may break, generally ruining the results and requiring that the sequencing must be run again. An associated problem is that factors which may influence the temperature of the gel during electrophoresis may vary widely, making it difficult to control the temperature during electrophoresis accurately.

One method of the prior art has been for a researcher to "baby sit" the electrophoresis sequencing process, periodically checking the temperature to see if the glass is becoming too hot. Typically the researcher will check the temperature by hand, i.e., by feeling the surface of the glass plates. While this method of the prior art may achieve the objective of speeding up the electrophoresis process, it is subject to the drawbacks that it is inaccurate, unreliable, and of course occupies the time of the researcher.

Accordingly, it is an object of the invention to provide a method and system for performing electrophoresis under automated temperature control.

SUMMARY OF THE INVENTION

The invention provides a method of (and apparatus for) electrophoresis in which the gel temperature is controlled automatically. In a preferred embodiment, a sensor may measure a gel temperature and a processor may control a power supply for the electrophoresis process in response to that measurement. In a preferred embodiment, measurements may be made at predetermined times (e.g., periodically) and the processor may determine control settings for the power supply based on a preferred temperature for the electrophoresis process. In a preferred embodiment, the preferred temperature for the electrophoresis process may be a predetermined temperature which is chosen so that the electrophoresis process operates at or near the highest speed which is unlikely to break the glass plates.

BRIEF DESCRIPTION OF THE DRAWINGS

FIGS. 2A–2H are combined. FIGS. 2A–2H collectively form a block diagram of the power supply element of an embodiment of the invention.

DESCRIPTION OF THE PREFERRED EMBODIMENT

The invention may be used together with several different electrophoresis systems which are not disclosed in detail herein. It would be clear to one of ordinary skill in the art, after perusal of the specification, drawings and claims herein, that coupling of the circuitry disclosed herein to an electrophoresis system of common design would be a straight-forward task and would not require undue experimentation. Accordingly, a more detailed description is not included.

Electrophoresis System

Figure 1:
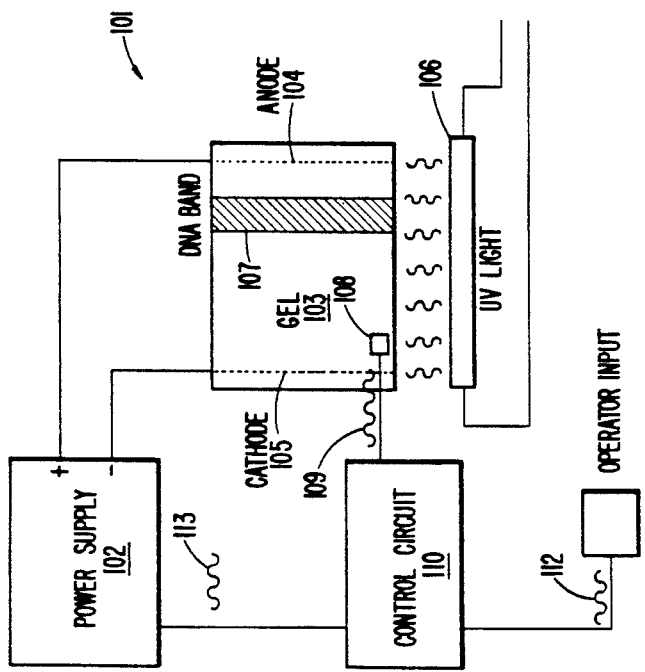
FIG. 1 is a block diagram of an embodiment of the invention.
Figure 2A:
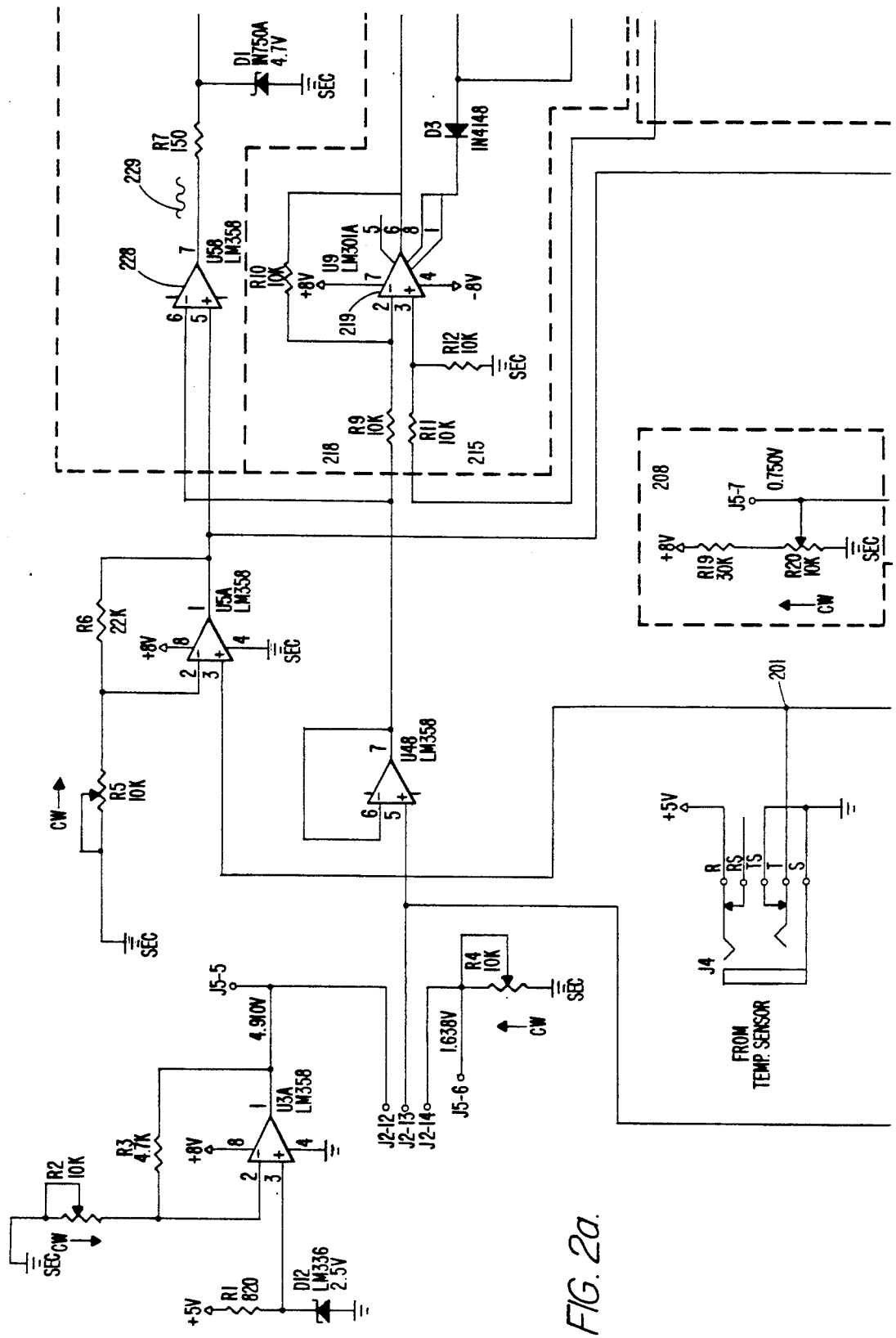
Figure 2B:
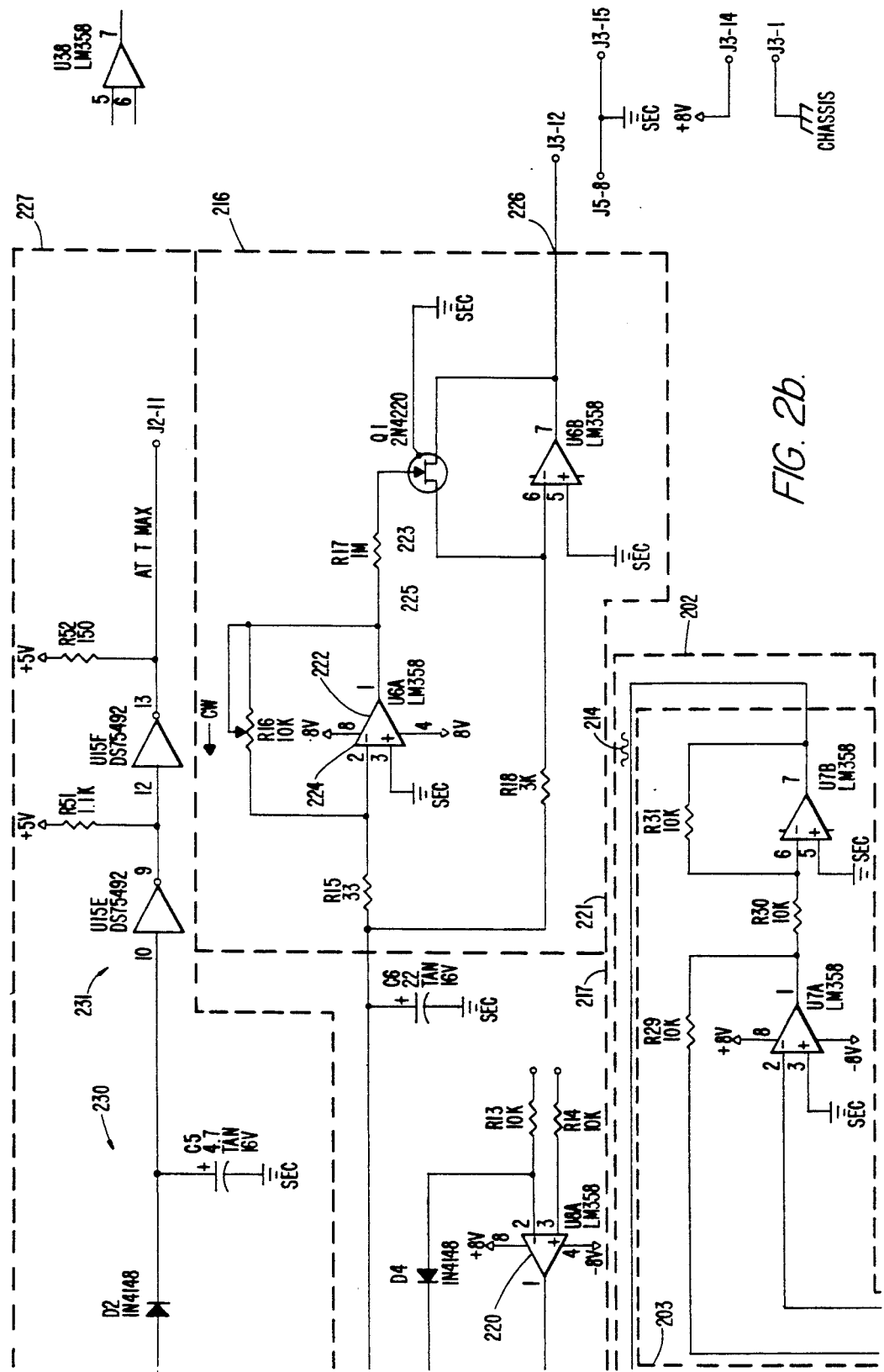
Figure 2C:
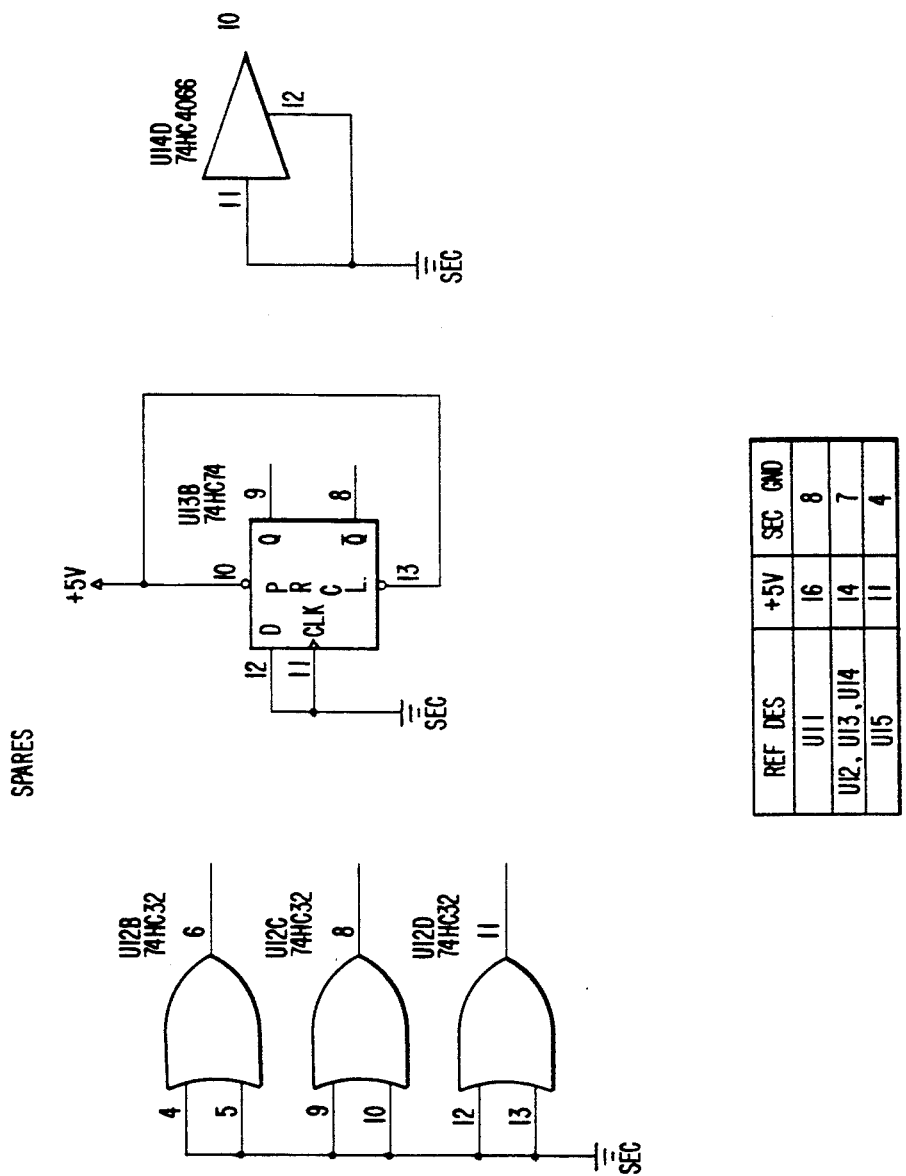
Figure 2D:
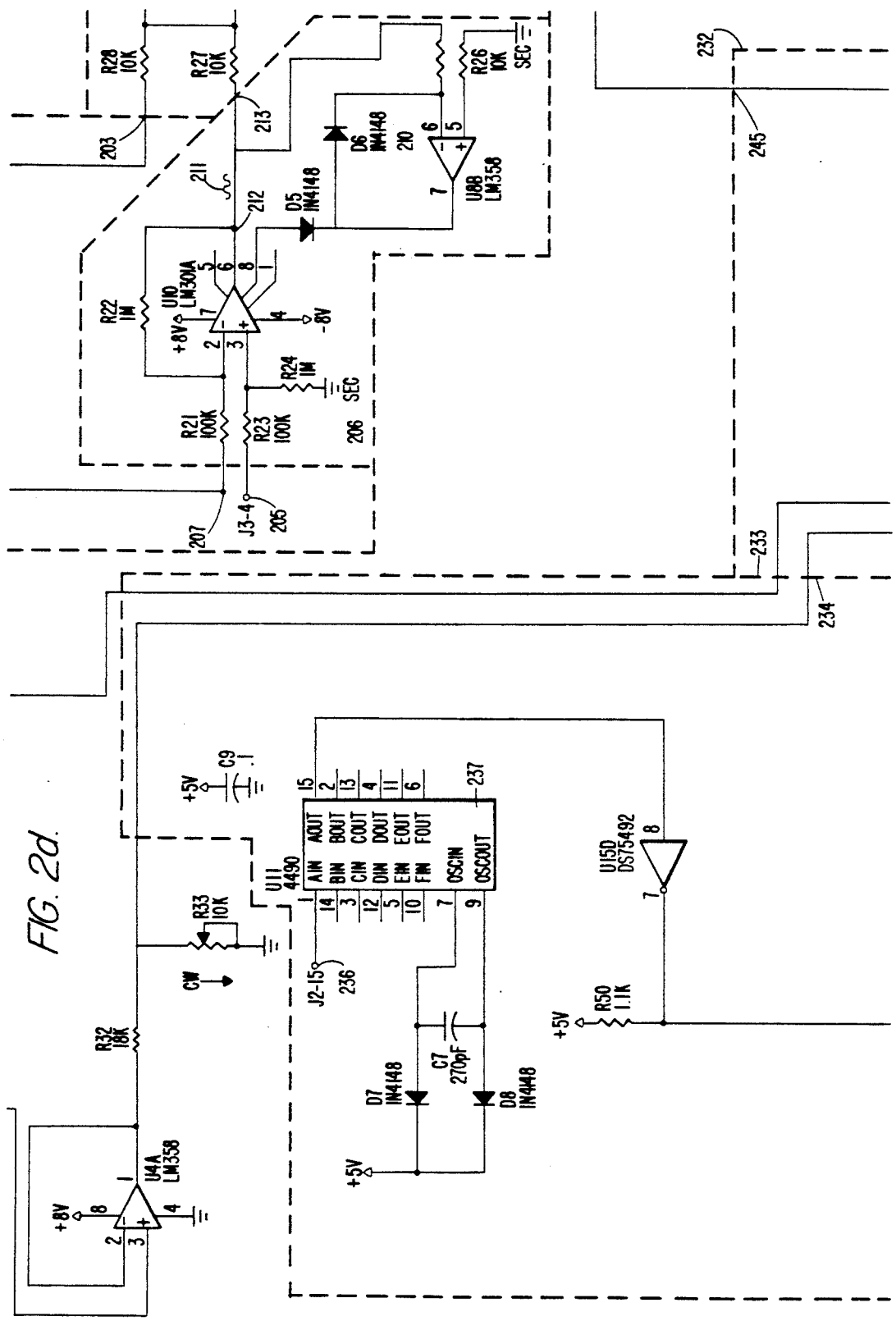
Figure 2E:
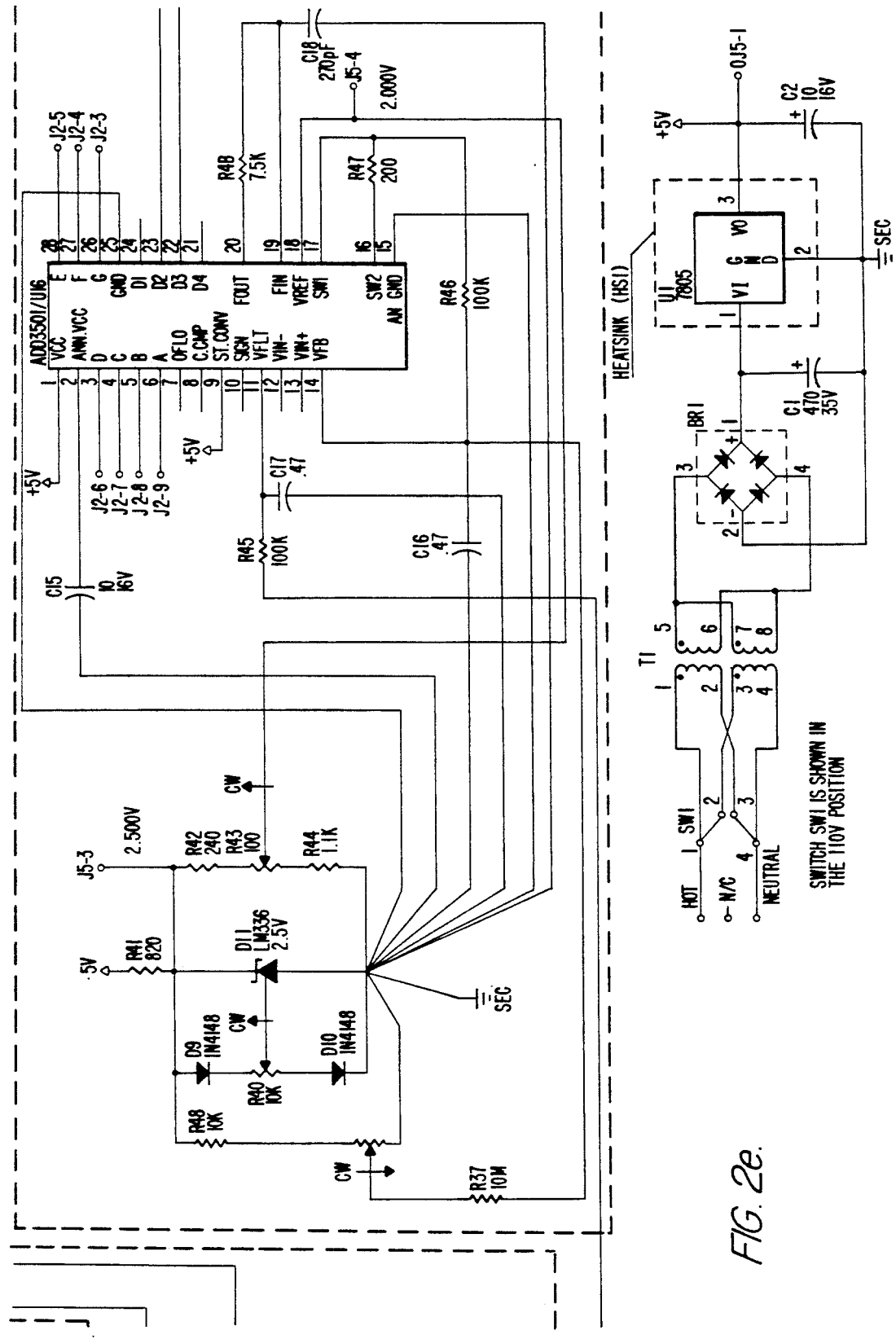
Figure 2F:
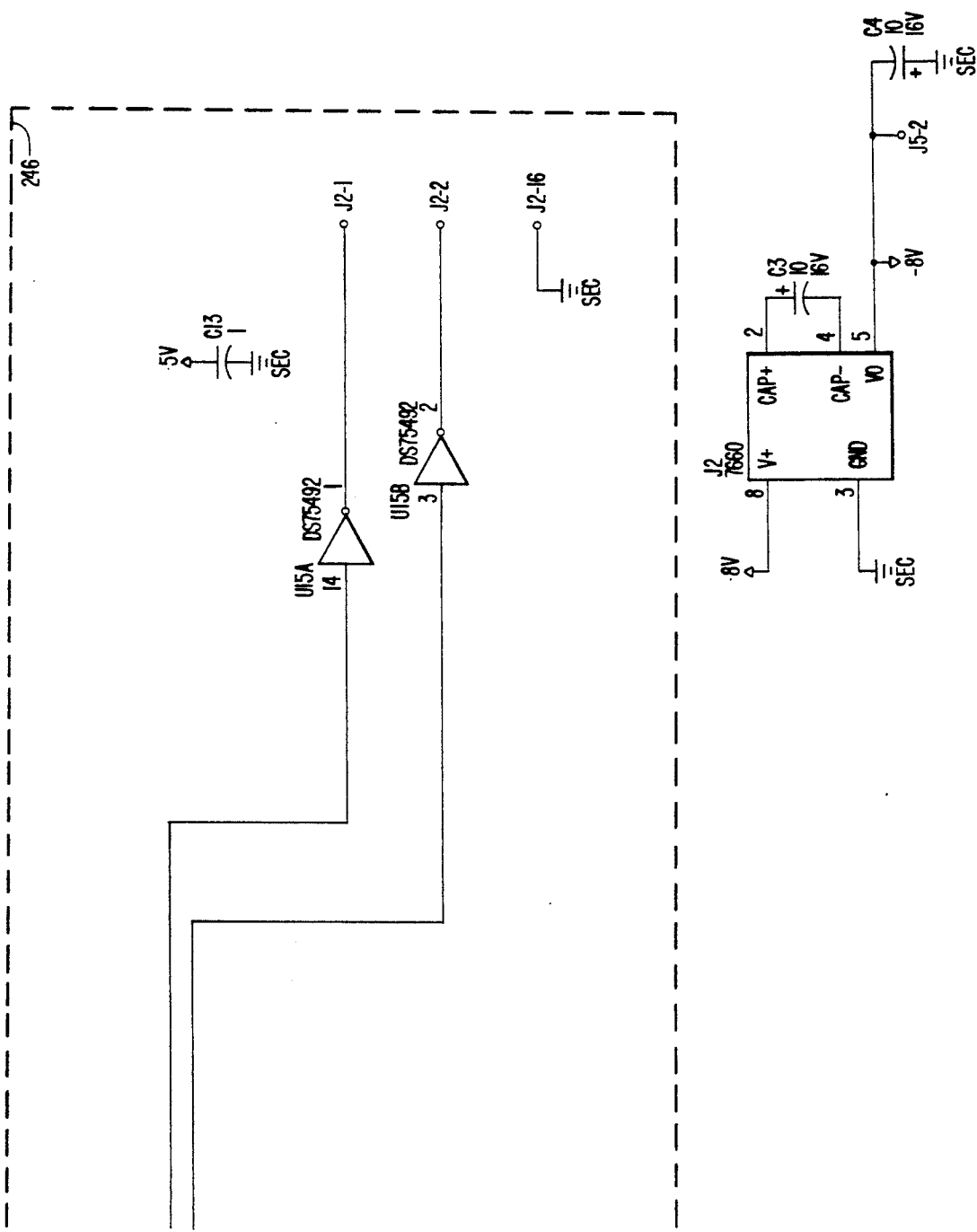
Figure 2G:
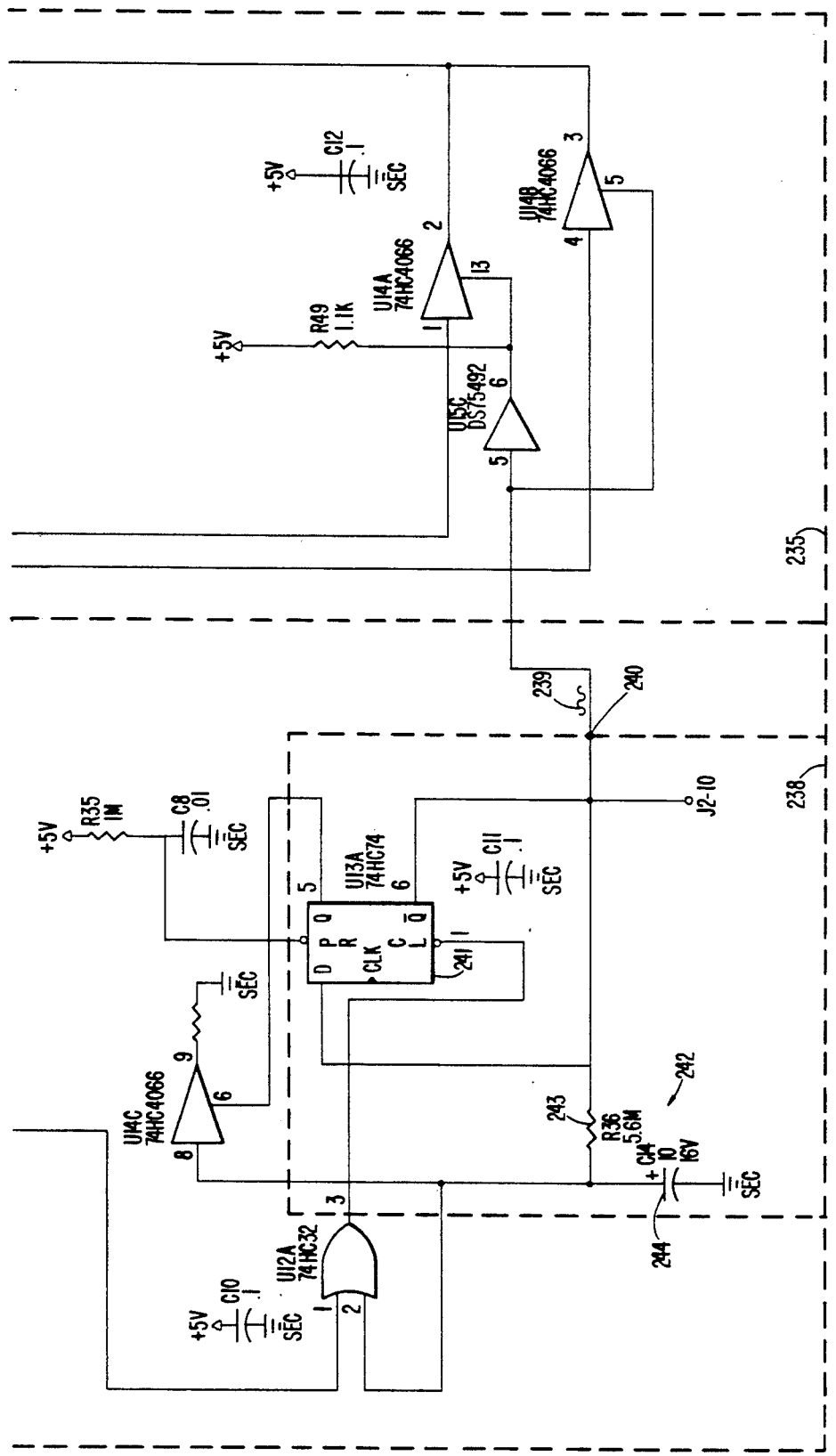

FIG. 1 is a block diagram of an embodiment of the invention.

An electrophoresis system 101 has a power supply 102 which supplies power for the electrophoresis process. In the electrophoresis system 101, a mixture of chemical substances to be separated is embedded in a gel 103 having an anode 104 and a cathode 105 coupled to the power supply 102. Typically, the gel 103 is sandwiched between a pair of glass plates (front and back) for physical support. The gel 103 may be soaked in a radioactive probe and an ultraviolet light 106 may be used to illuminate a DNA band 107 which has been separated by the electrophoresis process. A more detailed description of the electrophoresis process and apparatus for conducting the process may be found in "Electrophoresis: Theory, Techniques and Biochemical and Clinical Applications" (2d. ed.), by Anthony T. Andrews, published by Oxford University Press (New York, NY) in 1986, hereby incorporated by reference as if fully set forth herein.

A temperature sensor 108 may be disposed to measure the temperature of the gel 103. In a preferred embodiment, the temperature sensor 108 may be positioned on one of the glass plates, such as with adhesive tape. An sensor signal 109 from the temperature sensor 108 is coupled to a control circuit 110. An operator input device 111 may be disposed so that a human operator may indicate a desired temperature at which the electrophoresis process should operate. A setpoint signal 112 from the input device 111 is also coupled to the control circuit 110. The control circuit 110 compares the sensor signal 109 and the setpoint signal 112 and generates an adjustment signal 113, which is coupled to the power supply 102. The adjustment signal 113 adjusts the operation of the power supply 102 so as to maintain the temperature of the gel 103 at the desired temperature which was selected by the operator.

In a preferred embodiment, the power supply 102 may be like a power supply and control system disclosed in a copending application titled "ELECTROPHORESIS SYSTEM" application Ser. No. 498,201, Lyon & Lyon Docket No. 190/62, filed Mar. 23, 1990 in the name of Frank Cathel and Robert LeSchofs, hereby incorporated by reference as if fully set forth herein. In the specification for this invention, familiarity with that copending application is presumed; accordingly, the power supply 102 used in a preferred embodiment of this invention is not described in detail herein.

In a preferred embodiment, the power supply 102 may control the supplied power to the electrophoresis system 101 by comparing a voltage signal indicating measured output power with a setpoint voltage, as shown in copending application Ser. No. 498,201. In copending application Ser. No. 498,201, the setpoint voltage may be generated by a summing amplifier 418 (shown therein), comprising a summing node 433 (shown therein). In a preferred embodiment of this invention, the adjustment signal 113 may be coupled to that summing amplifier 418 at that summing node 433, so as to cause the control signal generated at an output of that summing amplifier 418 to be adjusted as indicated by the adjustment signal 113. Accordingly, the control circuit 110 may adjust the power output by the power supply 102 so as to maintain the temperature of the gel 103 at the desired temperature which was selected by the operator.

Control Circuit

Figure 2:
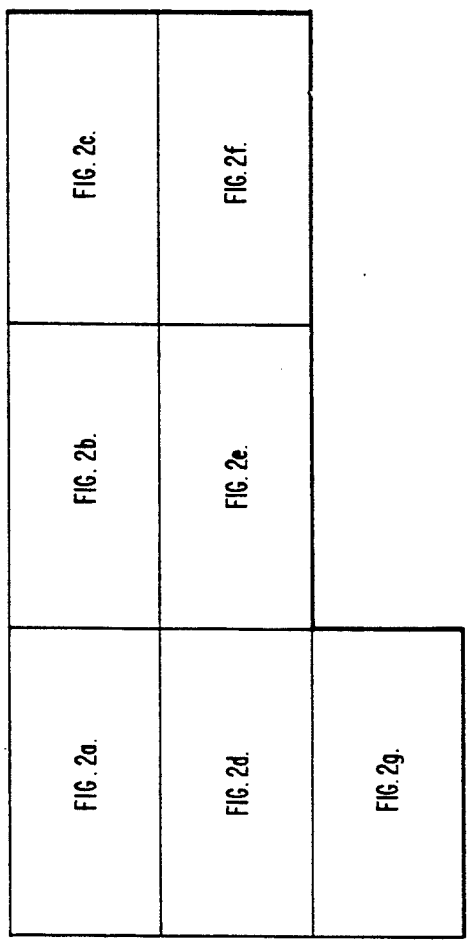
FIG. 2 is a drawing showing how

FIG. 2 is a drawing showing how FIGS. 2A–2H are combined. FIGS. 2A–2H collectively form a block diagram of the power supply element of an embodiment of the invention.

Clamp Circuit

The sensor signal 109 is output by the temperature sensor 108 at a node 201, which is coupled to a first input of a minimum output clamp circuit 202 at a first input 203 of a clamp circuit summing amplifier 204. In a preferred embodiment, the temperature sensor 108 may comprise a linear temperature sensor with about 10 millivolts per degree sensitivity, such as part number LM35CAH made by National Semiconductor.

A second input of the clamp circuit 202 is coupled to a signal indicating the output current of the power supply 102 at an output current node 205. The output current node 205 is coupled to a positive input of a clamp circuit differential amplifier 206, while a negative input of the clamp circuit differential amplifier 206 is coupled to a threshold node 207. The threshold node 207 is coupled to a threshold circuit 208, which supplies a voltage indicating a minimum current for the power supply 102, as is well known in the art. In a preferred embodiment, the clamp circuit differential amplifier 206 may comprise a set of two op-amps 209 and 210 arranged in an amplifier configuration for negative swing only, the structure of which is well known in the art, such as part numbers LM301A and LM358 respectively, made by National Semiconductor.

The clamp circuit differential amplifier 206 generates a clamping signal 211 at a clamping node 212, indicating how far the actual current for the power supply 102 is below the minimum current for the power supply 102. The clamping node 212 may be coupled to a second input 213 of the clamp circuit summing amplifier 204, so as to sum the clamping signal 211 with the sensor signal 109, as is well known in the art. This causes the power supply 102 to clamp at a minimum output current, as is well known in the art.

The clamp circuit 202 generates an adjusted sensor signal 214 at an output of the clamp circuit summing amplifier 204. The output of the clamp circuit summing amplifier 204 is coupled to a first input 215 of a temperature feedback amplifier 216 at a positive input of a temperature differential amplifier 217.

Temperature Feedback Circuit

The setpoint signal 112 output by the input device 111 is coupled to a second input 218 of the temperature feedback amplifier 216 at a negative input of the temperature differential amplifier 217. In a preferred embodiment, the temperature differential amplifier 217 may comprise a set of two op-amps 219 and 220 arranged in an amplifier configuration for negative swing only, the structure of which is well known in the art, such as part numbers LM301A and LM358 respectively, made by National Semiconductor.

An output of the temperature differential amplifier 217 is coupled to an input of a temperature nonlinear amplifier 221. The temperature nonlinear amplifier 221 may comprise an amplifier op-amp 222 coupled in an amplifier feedback configuration with an amplifier transistor 223 coupled between a negative input 224 and an output 225 of the amplifier op-amp 222. In a preferred embodiment, the amplifier op-amp 222 may comprise part number LM358 made by National Semiconductor and the amplifier transistor 223 may comprise part number 2N4220 made by Motorola.

The temperature feedback amplifier 216 compares the adjusted sensor signal 214 with the setpoint signal 112 and generates the adjustment signal 113 at an output 226 of the temperature nonlinear amplifier 221, which is coupled to the power supply 102 like the power supply and control system shown in copending application Ser. No. 498,201, at the summing node 433 (shown therein) of the summing amplifier 418 (shown therein).

In a preferred embodiment, the output of the temperature differential amplifier 217 indicates the magnitude of the difference between the adjusted sensor signal 214 and the setpoint signal 112, and the temperature nonlinear amplifier 221 amplifies that difference by an amount which varies with variable magnitude. This causes the power supply 102 to increase the current (and thus the temperature of the gel 103) by large amounts when the difference is large and by only small amounts when the difference is small (i.e., when the actual temperature of the gel 103 is near the desired temperature).

External Heating Indicator

The sensor signal 109 and the setpoint signal 112 are also coupled to an input of an indicator circuit 227, at a positive and a negative input of an indicator comparator 228, respectively. The indicator comparator 228 thus generates an indicator signal 229 which will be a high voltage when the actual temperature of the gel 103 exceeds the desired temperature, and a low voltage otherwise. The indicator signal 229 is coupled by means of a filter 230 and a buffer 231, to an external indicator (not shown) such as a light-emitting diode. The external indicator (not shown) will thus show approximately when the gel 103 has reached the desired temperature and is no longer being heated continuously.

Temperature Display

The sensor signal 109 and the setpoint signal 112 are also coupled to a display circuit 232, at a first input 233 and a second input 234 respectively of a display mux 235. An external control such as a push button (not shown) generates a display select signal which is coupled to a display select node 236. The display select node 236 is coupled by means of a debounce circuit 237 to a one-shot 238, which generates a mux control signal 239 at an output node 240. The mux control signal 239 is coupled to a control input of the display mux 235, which selects either the sensor signal 109 or the setpoint signal 112 for output.

In a preferred embodiment, the display mux 235 may be set to display the actual temperature (as indicated by the sensor signal 109) in normal operation, but to display the desired temperature (as indicated by the setpoint signal 112) when the push button (not shown) is pressed. In a preferred embodiment, the one-shot 238 may comprise a D-type flipflop 241 such as part number 74HC74 made by Texas Instruments, configured with a resistor-capacitor circuit 242 comprising a 5.6 megaohm resistor 243 and a 10 microfarad capacitor 244, so as to generate a pulse of about one minute duration, as is well known in the art.

An output 245 of the display mux 235 is coupled to a digital display (not shown) by means of a display driver 246. In a preferred embodiment, the display driver 246 may comprise an A/D converter and a display driver combined in one circuit, the structure of which is well known in the art, such as part number ADD3501 made by National Semiconductor. The digital display (not shown) is thus able to display numeric values of the actual temperature and the desired temperature to a human operator.

Alternative Embodiments

While preferred embodiments are disclosed herein, many variations are possible which remain within the concept and scope of the invention, and these variations would become clear to one of ordinary skill in the art after perusal of the specification, drawings and claims herein.

We claim:

1. An electrophoresis system for separating charged chemical substances, comprising
   means for applying an electrical potential to a mixture of said charged chemical substances;
   means for sensing a temperature of said mixture; and
   means for altering said electrical potential in response to said temperature;
   wherein said means for sensing a temperature operates at predetermined times.

2. An electrophoresis system for separating charged chemical substances, comprising
   means for applying an electrical potential to a mixture of said charged chemical substances;
   means for sensing a temperature of said mixture; and
   means for altering said electrical potential in response to said temperature;
   wherein said means for sensing a temperature operates periodically.

3. An electrophoresis system as in claim 1 or 2, comprising
   means for generating a control signal indicating a level of power supply; and
   means for controlling said means for altering in response to said control signal.

4. An electrophoresis system as in claim 1 or 2, wherein said means for altering is capable of altering said electrical potential to achieve a preferred temperature for said mixture.

5. An electrophoresis system as in claim 4, wherein said preferred temperature is a predetermined fixed temperature.

6. An electrophoresis system as in claim 4, wherein said preferred temperature is chosen so that electrophoresis of said mixture occurs at a highest practical speed.

7. An electrophoresis method for separating charged chemical substances, comprising the steps of
   applying an electrical potential to a mixture of said charged chemical substances;
   sensing a temperature of said mixture; and
   altering said electrical potential in response to said temperature;
   wherein said step of sensing a temperature occurs at predetermined times.

8. An electrophoresis method for separating charged chemical substances, comprising the steps of
   applying an electrical potential to a mixture of said charged chemical substances;
   sensing a temperature of said mixture; and
   altering said electrical potential in response to said temperature;
   wherein said step of sensing a temperature occurs periodically.

9. An electrophoresis method as in claim 7 or 8, comprising the steps of
   generating a control signal indicating a level of power supply; and
   controlling said means for altering in response to said control signal.

10. An electrophoresis method as in claim 7 or 8, wherein said step of altering achieves a preferred temperature for said mixture.

11. An electrophoresis method as in claim 10, wherein said preferred temperature is a predetermined fixed temperature.

12. An electrophoresis method as in claim 10, wherein said preferred temperature is chosen so that electorphoresis of said mixture occurs at a highest practical speed.

13. An electrophoresis system for separating charged chemical substances, comprising
   an input device;
   a power supply coupled to a mixture of said charged chemical substances, said power supply having a power supply output sensor node;
   a temperature sensor coupled to said mixture, said temperature sensor being capable of operating at predetermined times;
   a clamp circuit coupled to said temperature sensor and to said power supply output sensor node;
   a temperature feedback amplifier coupled to said clamp circuit and to said input device, said temperature feedback amplifier having an output coupled to said power supply.

14. An electrophoresis system as in claim 13, comprising
   an external indicator coupled to said temperature sensor.

15. An electrophoresis system as in claim 13, comprising
   an external indicator coupled to said input device and to said temperature sensor.

16. An electrophoresis system as in claim 13, comprising
   an external indicator capable of displaying when said mixture of said charged chemical substances is not being heated continuously.

17. An electrophoresis system as in claim 13, wherein said clamp circuit comprises
   a threshold circuit;
   a clamp circuit differential amplifier coupled to said power supply and to said threshold circuit; and
   a clamp circuit summing amplifier coupled to said temperature sensor.

18. An electrophoresis system as in claim 13, wherein said clamp circuit comprises a differential amplifier having a plurality of op-amps disposed in an amplifier configuration for negative swing only.

19. An electrophoresis system as in claim 13, wherein said temperature feedback amplifier comprises
   a temperature differential amplifier coupled to said clamp circuit; and
   a temperature nonlinear amplifier.

20. An electorphoresis system as in claim 13, wherein said temperature feedback amplifier comprises a differential amplifier having a plurality of op-amps disposed in an amplifier configuration for negative swing only.

21. An electrophoresis system as in claim 13, wherein said temperature feedback amplifier comprises
   a temperature nonlinear amplifier comprising an op-amp disposed in an amplifier feedback configuration with a negative input and an output, and with an amplifier transistor coupled between said negative input and said output.

* * * * *

UNITED STATES PATENT AND TRADEMARK OFFICE
CERTIFICATE OF CORRECTION

PATENT NO. : 5,328,581
DATED : July 12, 1994
INVENTOR(S) : Joseph Sorge

It is certified that error appears in the above-indentified patent and that said Letters Patent is hereby corrected as shown below:

On column 2, line 37, replace "radioactive probe" with —fluorescent tag—.

Signed and Sealed this

Eighteenth Day of June, 1996

Attest:

BRUCE LEHMAN

*Attesting Officer*   *Commissioner of Patents and Trademarks*